(12) United States Patent
Imanishi et al.

(10) Patent No.: US 7,180,468 B2
(45) Date of Patent: Feb. 20, 2007

(54) OBJECT DETECTING DEVICE

(75) Inventors: Osamu Imanishi, Otsu (JP); Mataichi Kurata, Otsu (JP)

(73) Assignee: Optex Co., Ltd., Shiga (JP)

( * ) Notice: Subject to any disclaimer, the term of this patent is extended or adjusted under 35 U.S.C. 154(b) by 0 days.

(21) Appl. No.: 10/548,083

(22) PCT Filed: Mar. 8, 2004

(86) PCT No.: PCT/JP2004/002994

§ 371 (c)(1),
(2), (4) Date: Sep. 6, 2005

(87) PCT Pub. No.: WO2004/081609

PCT Pub. Date: Sep. 23, 2004

(65) Prior Publication Data

US 2006/0170547 A1    Aug. 3, 2006

(30) Foreign Application Priority Data

Mar. 11, 2003 (JP) ............................. 2003-064445

(51) Int. Cl.
*H01Q 1/42* (2006.01)
(52) U.S. Cl. ................. 343/872; 343/753; 343/909; 343/911 R
(58) Field of Classification Search ................. 343/753, 343/754, 757, 872, 909, 911 R, 911 L
See application file for complete search history.

(56) References Cited

U.S. PATENT DOCUMENTS

| | | | | |
|---|---|---|---|---|
| 2,842,760 A | * | 7/1958 | McLucas | 342/53 |
| 3,176,288 A | * | 3/1965 | Wyatt | 342/58 |
| 3,316,549 A | * | 4/1967 | Hallendorff | 342/77 |
| 6,791,499 B2 | * | 9/2004 | Nakamura et al. | 343/702 |
| 6,947,003 B2 | * | 9/2005 | Huor | 343/770 |

FOREIGN PATENT DOCUMENTS

| | | |
|---|---|---|
| JP | 5-223634 A | 8/1993 |
| JP | 7-110375 A | 4/1995 |
| JP | 11-167678 A | 6/1999 |
| JP | 2000-65949 A | 3/2000 |
| JP | 2002-82178 A | 3/2002 |

* cited by examiner

*Primary Examiner*—Tho Phan
(74) *Attorney, Agent, or Firm*—Sughrue Mion, PLLC (57) ABSTRACT

To provide an object detecting device having a capability of sufficiently adjusting the detection areas to suit to the environment in which it is installed, the object detecting device includes an antenna AT for emitting a detecting beam to the detection areas and receiving a portion of the detecting beam which has been reflected from the detection areas, and adjusting covers 6 and 7 covering a front portion of the antenna AT and operable to adjust respective figurations of the detection areas. The adjusting covers 6 and 7 are selectively fitted one at a time to the front portion of the antenna AT for defining a different figuration of the detection areas. When one of the adjusting covers, that is, the cover 6 that is formed with a pair of cutouts 63 and 63 for suppressing the side lobe of the detecting beam is selectively used, the detection areas can be defined having no unnecessary detection areas.

5 Claims, 7 Drawing Sheets

OBJECT DETECTING DEVICE

This application is a 371 of PCT/JP04/02994, filed Mar. 8, 2004.

FIELD OF THE INVENTION

The present invention generally relates to an object detecting device of a kind utilizing microwaves generally employed in association with an automatic door system or for security monitoring purpose and, more particularly, to the object detecting device in which the detection area, from which an object such as, for example, a human body is to be detected, can be properly adjusted in dependence on the environment for installation of the object detecting device.

BACKGROUND ART

The object detecting device for an automatic door system or for security monitoring purpose is generally so designed that while a detection wave in the form of a microwave is emitted towards a detection area from which the presence or absence of an object such as, for example, one or more human bodies is desired to be detected, the object can be detected in terms of a change in frequency brought about by the Doppler effect when a portion of the detection wave reflected from the object is received.

As an antenna for defining the detection area for such an object detecting device, a horn antenna has hitherto been employed largely. However, since the horn antenna unit including the horn antenna itself and peripheral parts represents a shape generally similar to the shape of a trumpet and is therefore bulky in size, the use of the horn antenna tends to result in increase in size of the object detecting device and, therefore, the handling of the object detecting device as a whole during the installation thereof tends to be complicated and time-consuming.

Also, it is a general practice that depending on the environment in which the object detecting device is set up, the detection area that can be covered by the object detecting device is adjusted to a relatively wide detection area where the object detecting device is set up in a door assembly of a relatively large width, to a relatively narrow detection area where the object detecting device is set up in a door assembly of a relatively small width. With the standard object detecting device utilizing the horn antenna, the adjustment of the detection area is carried out by moving adjustable walls, which are disposed on left and right sides of the horn antenna, respectively, for the adjustment of the coverage of the object detecting device, or by installing the adjustable walls at predetermined or required positions, followed by turning the horn antenna unit through an angle of 90°. Such procedures for adjusting the detection area are indeed complicated and time-consuming.

In order to alleviate such problems and inconveniences as discussed above, the object detecting device assembled compact in size and designed to facilitate the adjustment of the detection area has been suggested, in which a patch antenna prepared from a metallic foil is employed in place of the horn antenna discussed above. See, for example, the Japanese Laid-open Patent Publication No. 7-110375. According to this prior art, a dielectric lens, which may become a concave lens or a convex lens when turned 90°, is disposed rotatably in front of the patch antenna, such that the detection area can be easily and smartly adjusted to one of the wide and narrow detection areas when the dielectric lens is turned 90° in either direction.

However, even in the object detecting device utilizing the rotatable dielectric lens discussed above, since only one lens is turned to accomplish the adjustment of the detection area, the width to which the detection area can be adjusted is limited and it may often occur that no sufficient adjustment can be achieved.

In the case of the object detecting device, it is often observed that the microwave radiation beam emitted from the object detecting device contains small beam components, generally referred to as side lobes, on respective sides of a primary beam component intermediate between those side lobes. The presence of those side lobes means that some of the output of the primary beam component is lost to the side lobes, accompanied by reduction of the output of the primary beam to such an extent that unnecessary detection areas, which ought not to be formed, tend to be formed simultaneously with formation of the detection area defined by the primary beam. If those unnecessary detection areas are formed in the manner described above, and where the object detecting device is employed as a sensor for selectively detecting opening or closure of an automatic door, the object detecting device will detect a human body or any other object present within any of the unnecessary detection areas, posing the possibility that the automatic door will unnecessarily be closed or opened even though the automatic door ought not to be opened or closed. In addition, the detection area available includes two types, i.e., wide and narrow areas and no area intermediate between those wide and narrow areas can be formed. Therefore, the prior art is insufficient in that a variety of detection areas to cope with a variety of environments for installation of the object detection device cannot be available.

DISCLOSURE OF THE INVENTION

The present invention has been devised to substantially eliminate the foregoing problems and inconveniences and is intended to provide an object detecting device having a capability of sufficiently adjusting the detection area to suit to the environment in which it is installed.

Another important object is to provide the object detecting device of the type referred to above, in which no side lobe, which would otherwise attribute to the erroneous operation, will occur and in which the detection area can be adjusted to one of three types depending on the environment for installation of the object detecting device.

In order to accomplish the first mentioned object of the present invention, there is provided in accordance with the present invention, an object detecting device including an antenna for emitting a detecting wave to a detection area and receiving a portion of the detecting wave, which has been reflected from an object, and an adjusting cover covering the antenna and operable to adjust the detection area to a particular shape. As the adjusting cover, a plurality of adjusting covers are provided and are selected to adjust the detection area to one of a plurality of different shapes one at a time.

According to the present invention, adjustment of the detection area to one of the different shapes can be accomplished by selecting one of the adjusting covers used to cover the antenna. Accordingly, when one of the adjusting covers, each used to cover the antenna, and which are provided for adjusting the detection area to the different shapes one at a time, is selected to cover the antenna, the detection area of a desired or required shape that is sufficiently adjusted can easily be defined as necessary. Also, since the antenna itself is protected by the selected adjusting cover, there is no possibility that the orientation of the antenna may be displaced purposelessly and/or the antenna may be damaged and, therefore, the function of the antenna may not be lowered.

In a preferred embodiment of the present invention, one of the adjusting covers may include a disc shaped front wall and a peripheral wall extending rearwardly from a peripheral edge of the front wall. In this case, the front wall has opposite side portions depressed radially inwardly to define corresponding cutouts for suppressing side lobes of the detection wave emitted from the antenna.

According to this preferred feature, a relatively wide detection area (a wide area) can easily be set up. Moreover, generation of side lobes tending to occur at lateral portions of a primary beam component of the radiation beam of the detection wave emitted from the antenna can be forcibly suppressed by the presence of the cutouts. Accordingly, without the output of the primary beam being lowered, unnecessary detection areas, which ought not to be formed other than the detection area defined by the primary beam component, will not be formed. Thus, since no output of the primary beam component is lowered, the detection accuracy in the detection area is excellent and, accordingly, since no unnecessary detection area is formed, even when the object detecting device is used as a detection sensor for selectively opening or closing, for example, an automatic door assembly, the presence of a human body and/or an object within the unnecessary detection areas will never be detected, thereby eliminating an erroneous operation of the automatic door assembly, in which the automatic door is selectively opened or closed when it ought not to be opened or closed.

In another preferred embodiment of the present invention, another one of the adjusting covers may include a disc shaped front wall and a peripheral wall extending rearwardly from a peripheral edge of the front wall, in which case the front wall has a convex lens portion having a thickness progressively increasing from a position of the peripheral edge thereof towards the geometric center of the front wall.

According to this preferred feature, the presence of the convex lens portion allows the directionality of the detection wave, then passing through the convex lens portion, to be narrowed and, therefore, the detection area in the form of a spot (a spot area) having a relatively small depth can also be formed. This leads to the detection area that can be changed considerably.

In a further preferred feature, the antenna may be retained by a retaining member mounted rotatably on a sensor body and the adjusting cover may then be mounted on this retaining member.

According to this preferred feature, since the antenna and the adjusting cover can be fixed in position through the retaining member, turn of the adjusting cover is accompanied by rotation of the antenna to thereby change the shape of the detection area. Accordingly, where the adjusting cover having the cutouts defined therein is employed, turn of the antenna and the adjusting cover through 90° can result in the detection area to be oriented vertically so as to define the narrow area or transversely so as to define the wide area. Thus, selection of one of the wide area and the narrow area can be accomplished by changing the orientation of the single antenna, with no need to employ dedicated antenna to define the respective required detection areas, resulting in reduction in number of the component parts used and simplification of the structure. Also, by replacing the adjusting cover with an adjusting cover having the convex lens portion, the detection area can easily be adjusted to the spot area.

In a still further preferred embodiment of the present invention, the object detecting device may furthermore include a support base, a first holder mounted on the support base for rotation about a first axis, a second holder supported under the first holder for rotation about a second axis lying perpendicular to the first axis, and an antenna module for retaining the antenna and mounted on the second holder for rotation about a third axis lying perpendicular to the second axis.

According to this preferred feature, turn of the first holder about the first axis can result in adjustment of the detection area in leftward and rightward directions. On the other hand, turn of the second holder about the second axis can result in adjustment of the detection area in forward and rearward directions. Also, turn of the antenna module about the third axis can result in change of the orientation of the antenna with the detection area selected to, for example, one of the wide area and the narrow area. Thus, since the detection area can easily be adjusted in any one of three axes, the installing operation at the site of installation of the object detecting device can easily and quickly be performed.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

BEST MODE FOR CARRYING OUT THE INVENTION

Hereinafter a preferred embodiment of the present invention will be described in detail with reference to the accompanying drawings.

Figure 1:
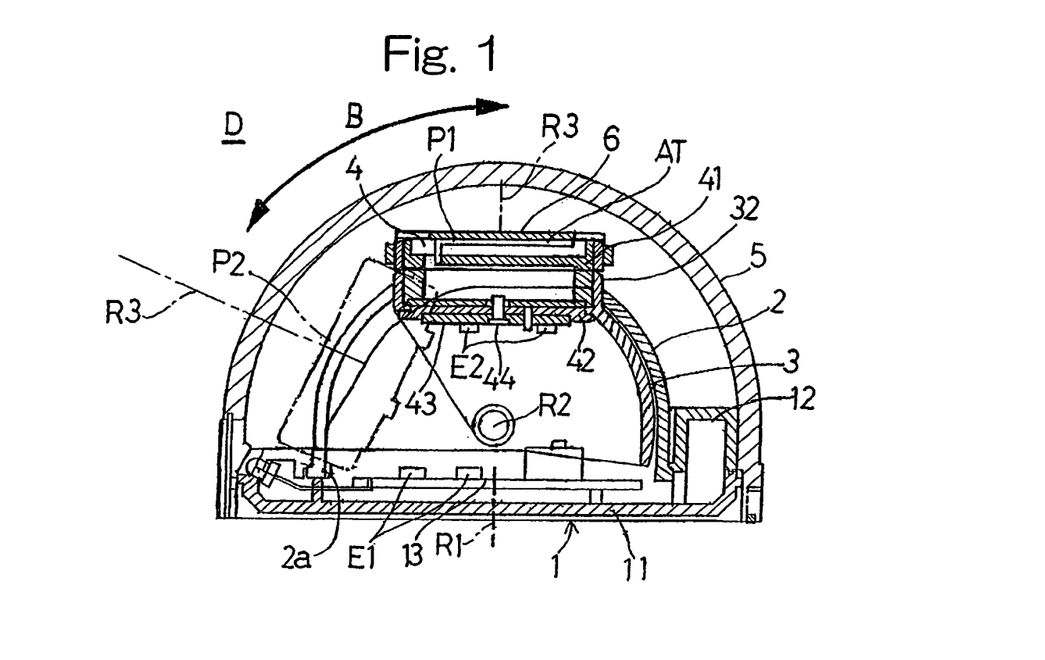
FIG. 1 is a transverse sectional view of an object detecting device according to a preferred embodiment of the present invention as viewed in a direction shown by the arrow I in FIG. 2.
Figure 2:
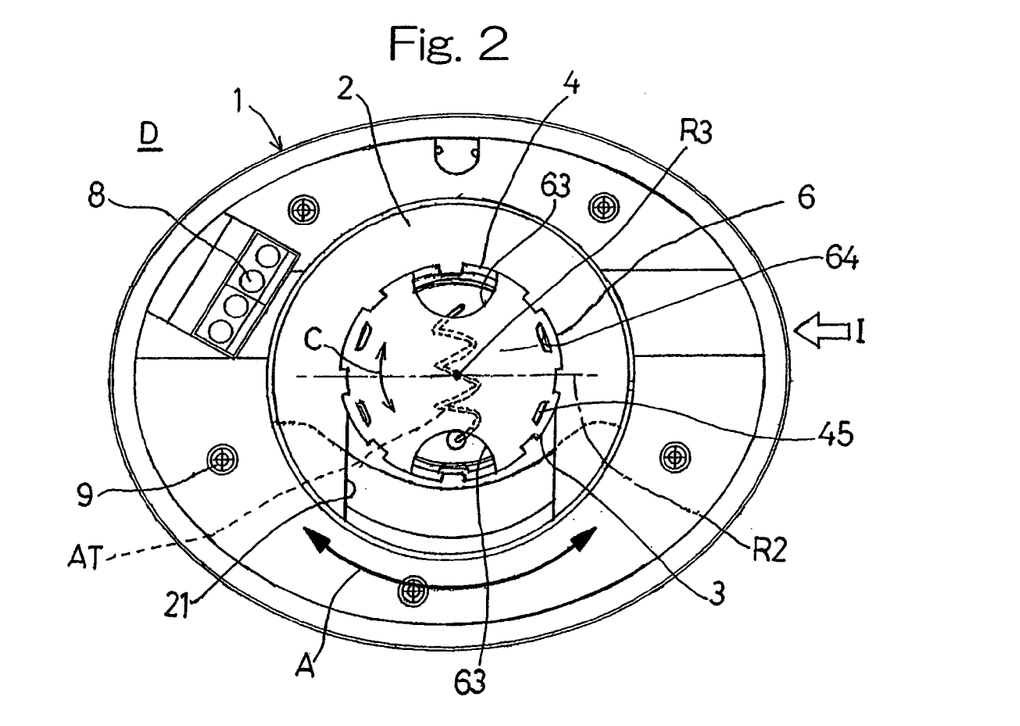
FIG. 2 is a front elevational view of the object detecting device shown in FIG. 1.

FIG. 1 illustrates in a transverse sectional representation, an object detecting device according to the preferred embodiment of the present invention as viewed in a direction shown by the arrow I in FIG. 2, while FIG. 2 illustrates a front elevational view of the object detecting device.

Referring particularly to FIG. 1, the object detecting device generally identified by D and designed in accordance with the present invention includes a support base 1, a first holder 2 (best shown in FIG. 3) supported above the support base 1 for rotation about a first axis R1 lying perpendicular to a bottom surface of the support base 1, a second holder 3 (best shown in FIG. 4) supported under the first holder 2 for rotation about a second axis R2 lying perpendicular to the first axis R1, and an antenna module 4 for holding an antenna AT for transmitting and receiving a detection wave and mounted on the second holder 3 for rotation about a third axis R3 lying perpendicular to the second axis R2.

Figure 3:
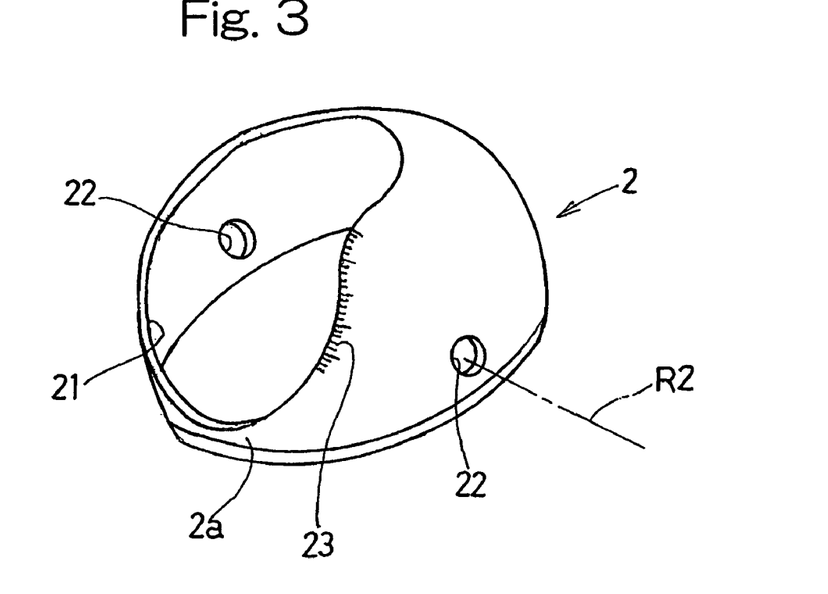
FIG. 3 is a perspective view showing a first holder employed in the object detecting device shown in FIGS. 1 and 2.
Figure 4:
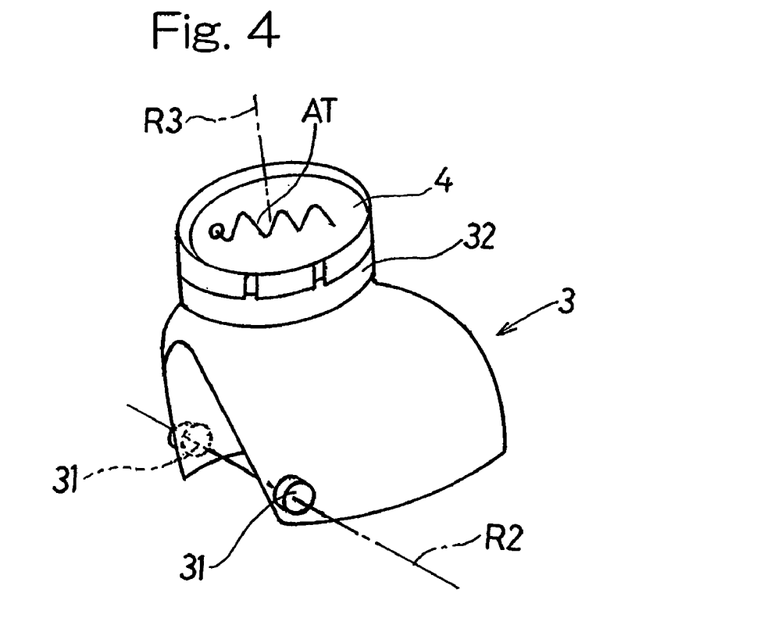
FIG. 4 is a perspective view showing a second holder employed in the object detecting device shown in FIGS. 1 and 2.

The support base 1 includes a base plate 11 for accommodating a circuit substrate 13 having electronic component parts E1 mounted thereon and adapted to be secured to an external member such as, for example, a transom or ceiling above an automatic door assembly, and an inner cover 12 for covering the base plate 11. The first holder 2 is so shaped as to represent a generally semispherical configuration as best shown in FIG. 3 and is supported above the support base 1 with a lower peripheral edge portion 2a movably sandwiched between the base plate 11 and the inner cover 12. The base plate 11 and the inner cover 12 are connected together by means of a plurality of, for example, five screws 9 as best shown in FIG. 2.

The second holder 3 (best shown in FIG. 4) positioned inside the first holder 2 and supported for rotation about the second axis R2 lying perpendicular to the first axis R1 is similarly so shaped as to represent a generally semispherical configuration. Means for supporting the second holder 3 inside the first holder 2 includes stud pins 31 and 31 protruding laterally outwardly from the second holder 3 in alignment with the second axis R2, which pins 31 and 31 are snap fitted into corresponding bearing holes 22 and 22 defined in the first holder 2 in alignment with the second axis R2.

As previously described, the antenna module 4 for transmitting and receiving a microwave, which is an example of the detection wave, is mounted atop the second holder 3 shown in FIG. 1 for rotation about the third axis R3 lying perpendicular to the second axis R2. This antenna module 4 includes a retaining member 41 for retaining the antenna AT and is fixed in position above the second holder 3 by means of a plurality of, for example, two set screws 44 with a top mount 32 of the second holder 3 sandwiched between the retaining member 41 and a back plate 42 of the second holder 3. Also, a circuit substrate 43 having electronic component parts E2 mounted thereon is secured to a rear surface of the back plate 42 of the second holder 3, and the antenna AT referred to above is employed in the form of a zigzag shaped, two dimensional wire as best shown in FIG. 2. This antenna module 4 is, when the second holder 3 is turned, movable within an opening 21, defined in the first holder 2, between a position P1, shown by the solid line in FIG. 1, and a position P2 shown by the phantom line in FIG. 1

The support base 1 referred to previously is covered by a doom shaped outer cover 5 made of a synthetic resin, with the first holder 2, the second holder 3 and the antenna module 4 consequently protected inside the doom shaped outer cover 5.

A first adjusting cover 6 made of a dielectric synthetic resin is mounted on the retaining member 41 so as to conceal the antenna AT and is utilized to adjust the shape of the detection area as will be described subsequently.

Figures 5A, 5B:
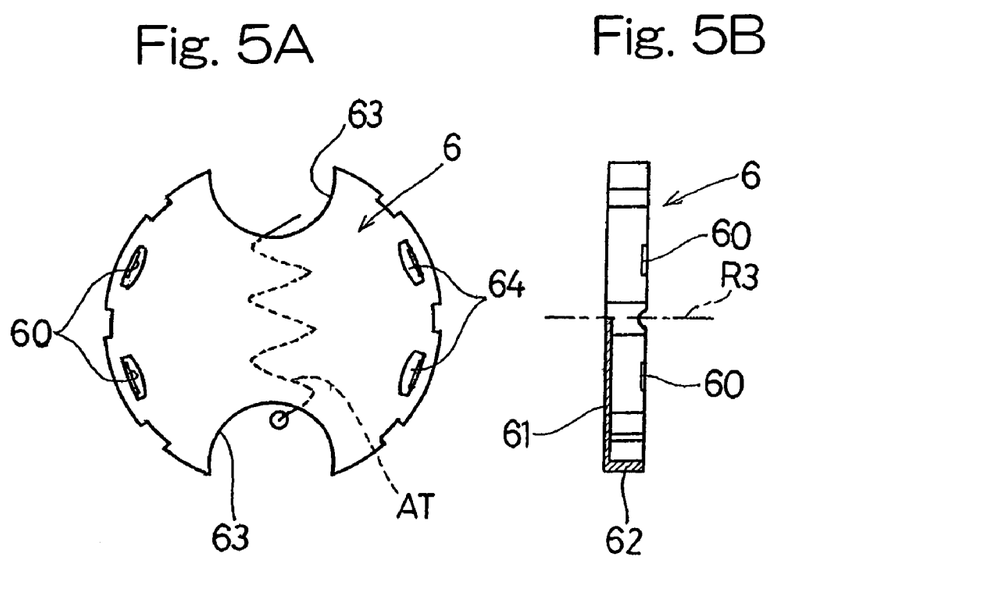
FIGS. 5A to 5D are front elevational views and partially sectioned side views, showing a first adjusting cover employed in the object detecting device.
Figure 5C:
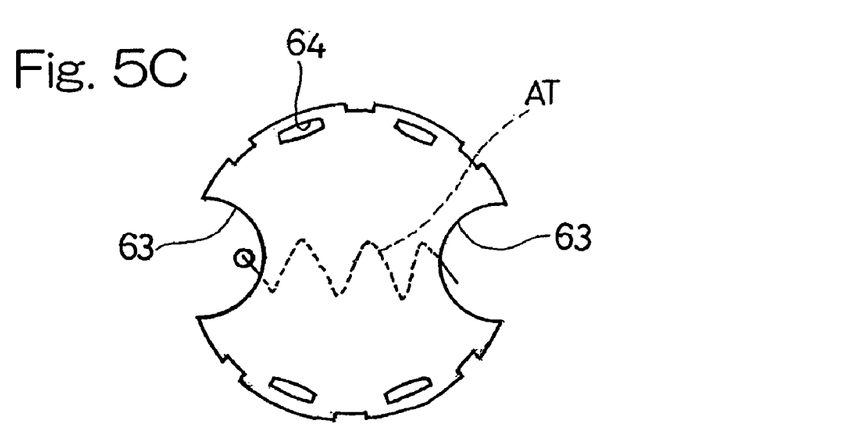
Figure 5D:
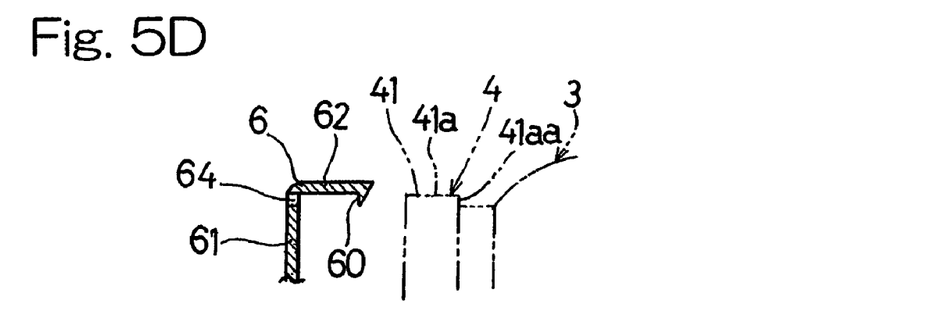

The first adjusting cover 6 is of such a shape as shown in FIG. 5. Referring particularly to FIG. 5B, the adjusting cover 6 is of a generally cap-like configuration including a disc shaped front wall 61 and a peripheral wall 62 protruding rearwardly from a peripheral edge of the front wall 61 and has opposite side portions of the front wall 61 thereof formed with a pair of cutouts 63 and 63 so as to be depressed radially inwardly as best shown in FIG. 5A. When this adjusting cover 6 is so mounted as to conceal the antenna AT retained by the retaining member 41 as best shown in FIG. 1, the side lobes of the detection wave emitted from the antenna AT can be suppressed by the cutouts 63 and 63, respectively. This adjusting cover 6 is formed by the use of any known molding technique and has a mounting means of a structure including, as best shown in FIG. 5D, a plurality of, for example, four engagement pawls 60 formed integrally with a lower end of the adjusting cover 6, which pawls 60 are adapted to be engaged with corresponding portions of a lower edge 41aa of a peripheral protrusion 41a of the retaining member 41. As best shown in FIGS. 5A and 5C, the front wall 61 of the adjusting cover 6 is provided with dies cutting holes 64 for the formation of the engagement pawls 60, at respective locations aligned with longitudinal directions of those engagement pawls 60.

Setting of the detection area for the object detecting device of the structure described hereinbefore is carried out in the following manner. Specifically, setting of the detection area in leftward and rightward directions is accomplished by turning the first holder 2 about the first axis R1 relative to the support base 1 shown in FIG. 1, in one of opposite directions shown by the arrow A in FIG. 2. On the other hand, setting of the detection area in forward and rearward directions is accomplished by turning (moving forwards or rearwards) the second holder 3 about the second axis R2 relative to the first holder 2, in one of opposite directions shown by the arrow B in FIG. 1. Setting of the wide area or the narrow area can be accomplished by turning the antenna module 4 with the adjusting cover 6 mounted thereon, about the third axis R3 relative to the second holder 3 in one of opposite directions shown by the arrow C to thereby change the orientation of the antenna AT.

Figure 6A:
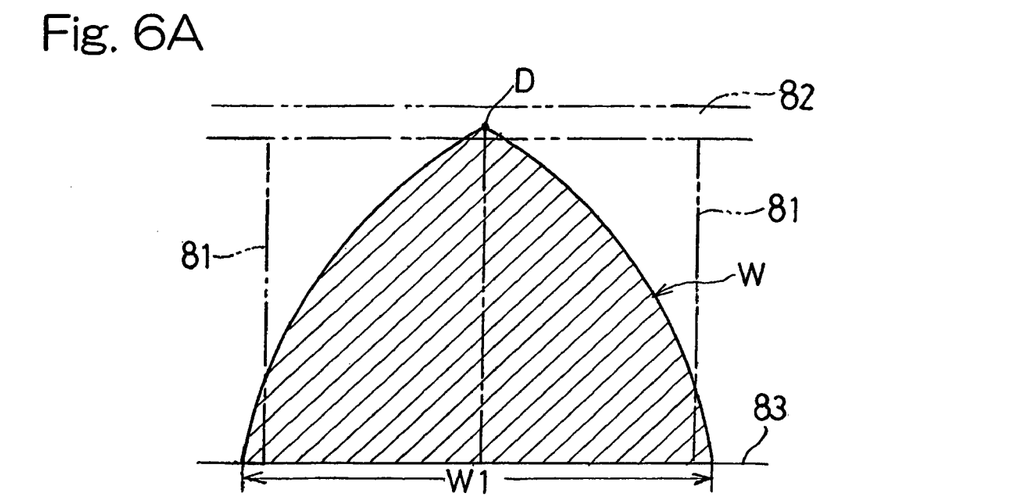
FIGS. 6A to 6C are schematic diagrams showing the figuration of a wide detection area.
Figure 6B:
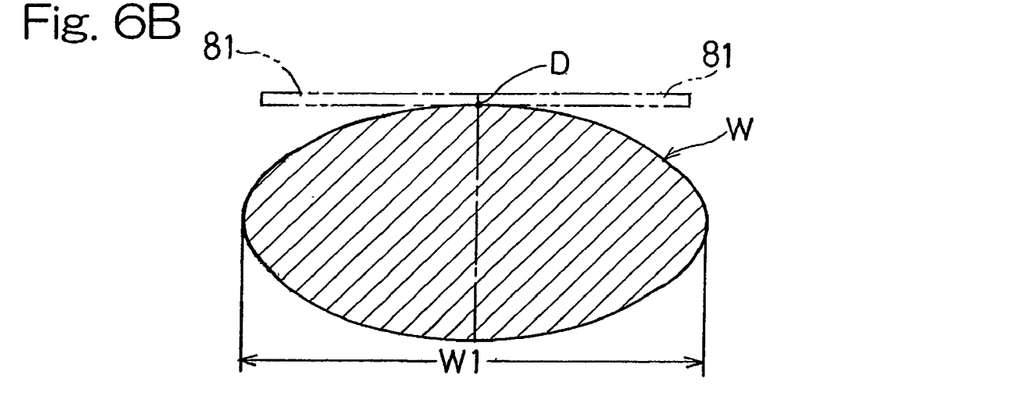
Figure 6C:
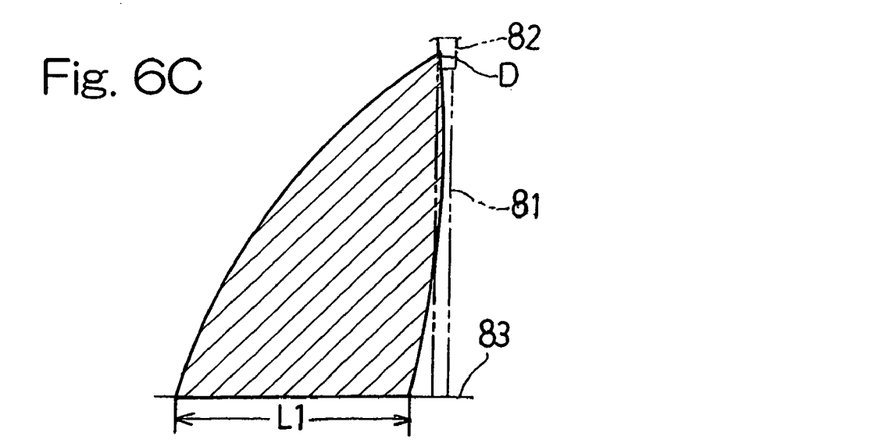

By way of example, the object detecting device D is mounted on a transom 82 above an automatic sliding door assembly 81 as shown in a front elevational view in FIG. 6. If by turning the antenna module 4 the adjusting cover 6 and the antenna AT are oriented vertically (in such case, the cutouts 63 63 are oriented upward and downward directions, respectively) as shown in FIG. 5A, the wide area W can be defined, which covers a large widthwise area forwardly of the position of installation of the object detecting device as shown in FIG. 6. The detection area represented by this wide area W represents a transversely elongated, substantially oval shape (as shown in FIG. 6B) when viewed from top, which oval shape has a width W1 (FIG. 6A) as measured on a floor 83 when viewed from front and, also, has a relatively small depth L1 (FIG. 6C) as measured on the floor 83 when viewed from laterally. Also, the side lobes, which tend to occur where the cutouts 63 and 63 are not employed in the adjusting cover 6, are suppressed and, therefore, no unnecessary detection area is formed outside the area W shown by the hatching. Thus, when the detection area is set to the wide area W, the object detecting device of the present invention can be suitably and conveniently employed in association with an automatic double door assembly.

Figure 7A:
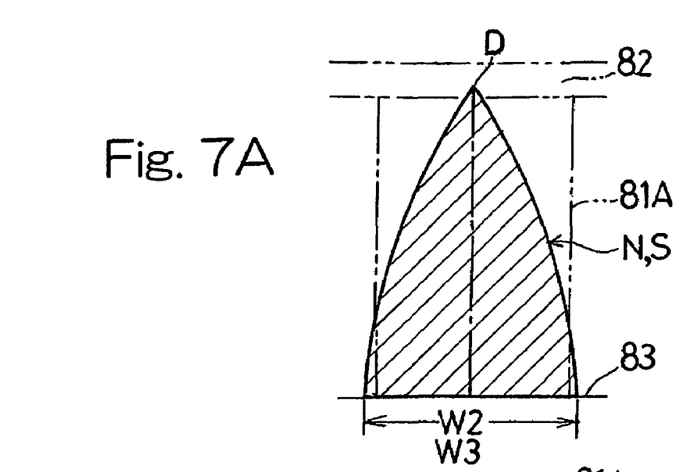
FIGS. 7A to 7C are schematic diagrams showing the figurations of a narrow detection area and a spot area.
Figure 7B:
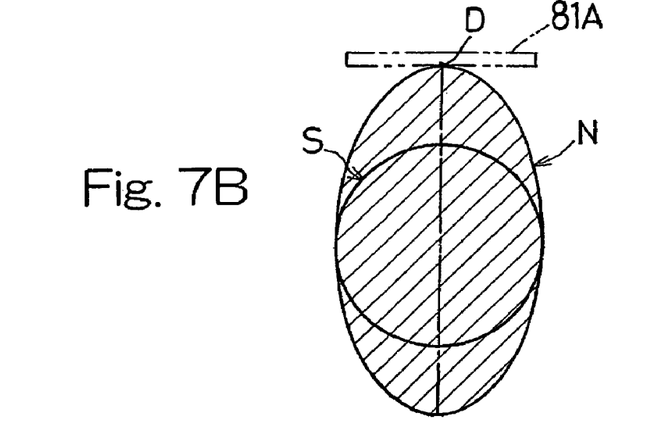
Figure 7C:
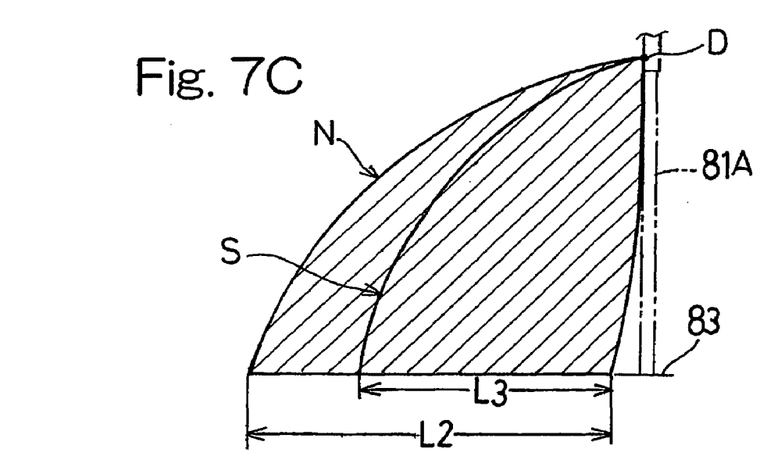

On the other hand, if the antenna module 4 is turned with the adjusting cover 6 and the antenna AT consequently oriented laterally (in such case, the cutouts 63 and 63 are oriented leftward and rightward directions, respectively) as shown in FIG. 5C, the narrow area N can be set, which has a relatively small width in front of the position of installation of the object detecting device. The detection area represented by this narrow area N represents a forwardly elongated, substantially oval shape (as shown in FIG. 7B) when viewed from top, which oval shape has a width W2 (FIG. 7A) as measured on the floor 83 when viewed from front, that is smaller than the width W1 shown in FIG. 6A, and also has a larger depth L2 (as shown in FIG. 7C) than the depth L1 shown in FIG. 6C when viewed from laterally. When the detection area is set to the narrow area N, the object detecting device of the present invention can be suitably and conveniently employed in association with an automatic single door or swinging door assembly.

Figure 8:
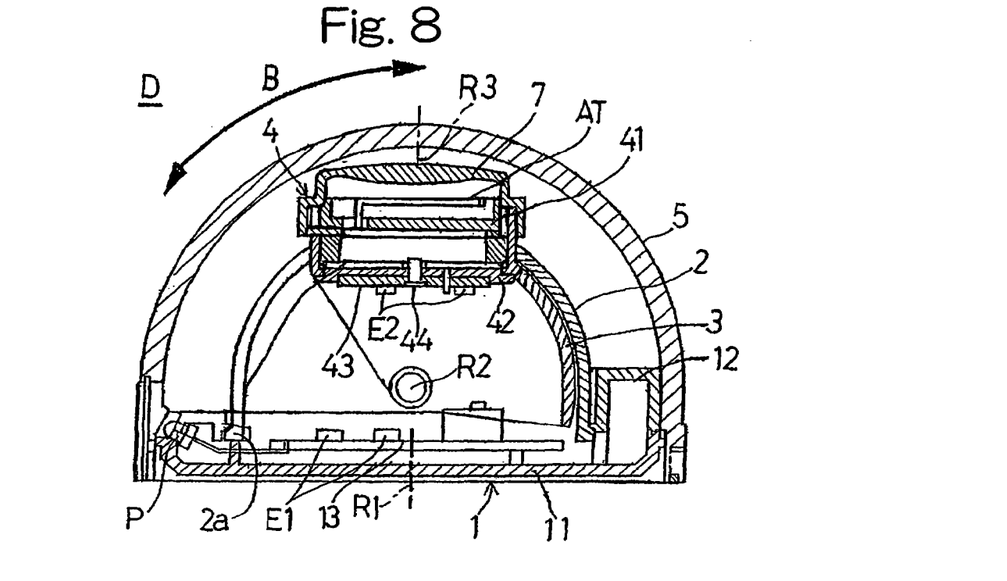
FIG. 8 is a transverse sectional view of the object detecting device having a second adjusting cover mounted thereon, as viewed in a direction shown by the arrow VIII in FIG. 9.
Figure 9:
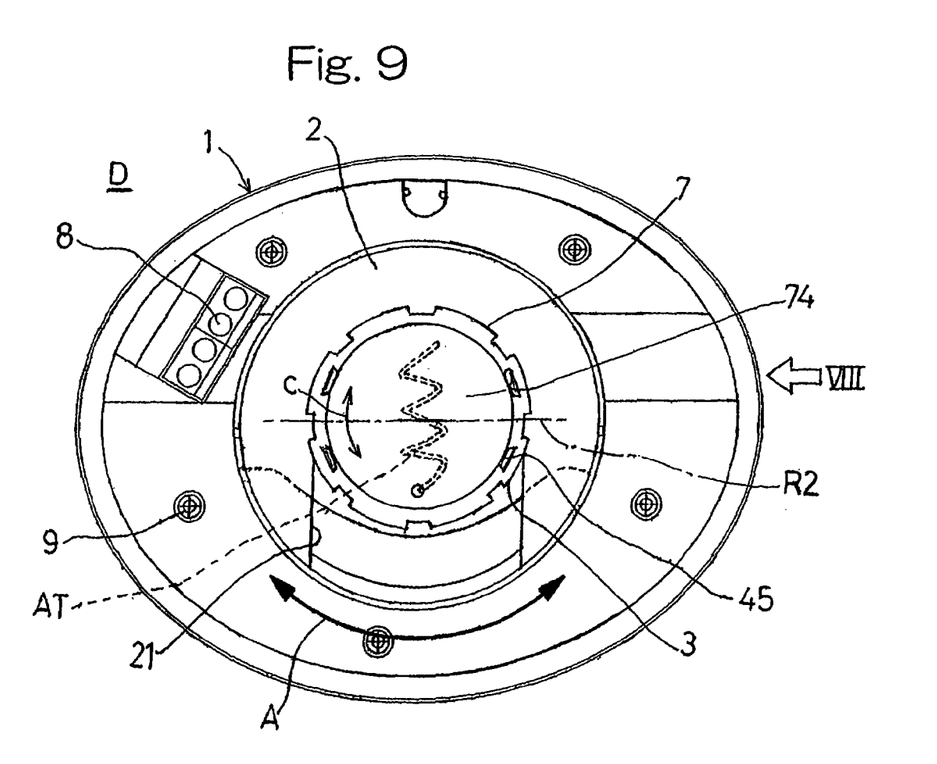
FIG. 9 is a front elevational view of the object detecting device shown in FIG. 8.
Figure 10A:
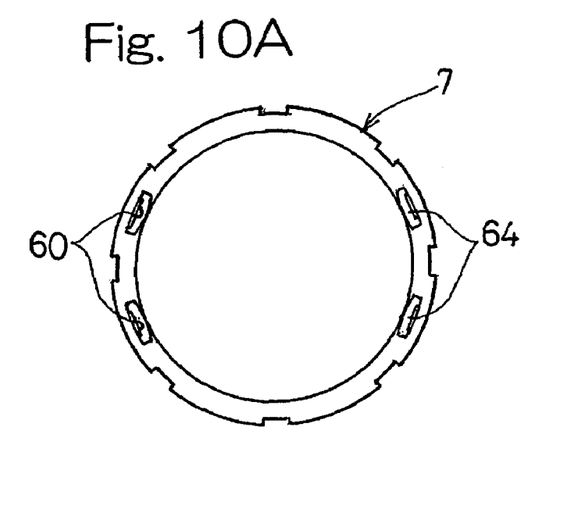
FIGS. 10A and 10B are a front elevational view of the second adjusting cover and a partially sectioned side view thereof, respectively.
Figure 10B:
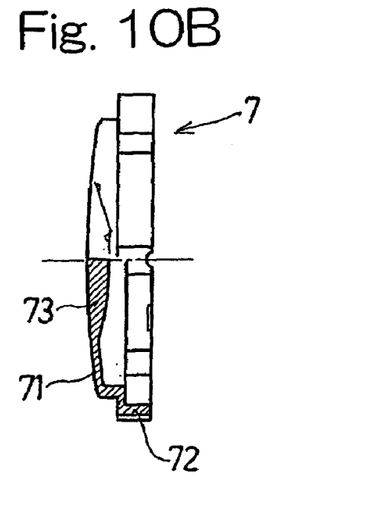

A second adjusting cover in accordance with the present invention is shown in FIG. 8. In a manner similar to the first adjusting cover 6 shown in and described with reference to FIG. 5, this adjusting cover 7 is made of a dielectric material such as, for example, a synthetic resin and is of a generally cap-like configuration including, as shown in FIG. 10, a disc shaped front wall 71 and a peripheral wall 72 protruding rearwardly from a peripheral edge of the front wall 71 (best shown in FIG. 10B). The front wall 71 has a convex lens portion 73 (best shown in FIG. 10B) of a thickness progressively increasing from a position of the peripheral edge thereof adjacent a geometric center of the front wall 71 towards the geometric center of the front wall 71. It is to be noted that even when the second adjusting cover 7 is mounted, this adjusting cover 7 is engaged with the retaining member 41 of the antenna module 4 shown in FIG. 8 by means of engagement pawls 60 in a manner similar to that of the first adjusting cover 6.

Figure 11:
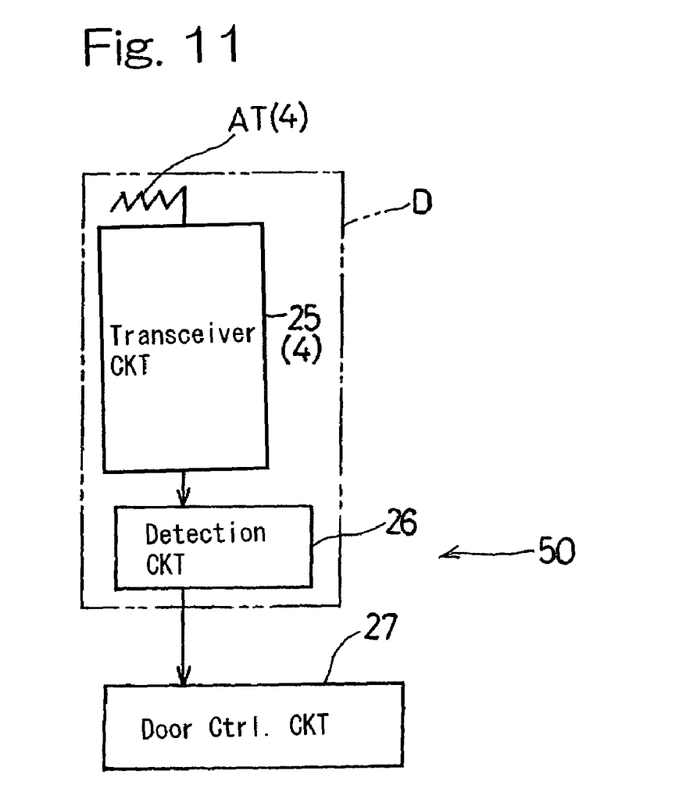
FIG. 11 is a circuit block diagram showing an object detecting system utilizing the object detecting device of the present invention.

When the adjusting cover 7 is mounted on the retaining member 41 of the antenna module 4, the spread of the microwave emitted is suppressed by the effect of a lens as the microwave passes through the convex lens portion 73, so that a spot area S, which is a detection area further narrower than the narrow area N, can be formed. In other words, as shown in FIG. 7A, the width W3 of the detection area as viewed from front is similar to the width W2 of the narrow area and represents a substantially round spot area S when viewed from top (best shown in FIG. 7B) in contrast to the vertically oval shape represented by the narrow area N. Also, when viewed from laterally, the detection area represents a shape having a depth L3, which is smaller than the depth L2 of the narrow area N as shown in FIG. 7C. As described above, selective use of one of the first and second adjusting covers 6 and 7 is effective to provide one of the three detection areas, i.e., the wide area W, the narrow area N and the spot area S.

Where the object detecting device of the present invention is used in association with an automatic door system 50 shown in FIG. 11, by the operation of a transceiver circuit 25 provided in the antenna module 4, a detection wave in the form of a microwave can be radiated from the antenna AT in the antenna module 4, and a portion of the detection wave reflected from an object such as, for example, a moving human body can be received by the transceiver circuit 25 through the antenna AT. In the event that the frequency of the detection wave reflected from the object and subsequently received by the transceiver circuit 25 changes by the Doppler effect, such change can be detected by a detecting circuit 26. A result of detection given by the detecting circuit 26 is then supplied to an external door control circuit 27 through a wiring connected with a connection terminal 8 shown in FIG. 2, to thereby control selective opening or closure of the automatic door.

If at this time the antenna module 4 with the first adjusting cover 6 mounted thereon is turned about the third axis R3 shown in FIG. 1 to position the antenna AT and the cutouts 63 and 63 in the adjusting cover 6 so as to orient in respective directions as shown in FIG. 5A, the detection area can be set to the wide area W as shown in FIG. 6. On the other hand, if the antenna AT and the cutouts 63 and 63 are positioned so as to orient as shown in FIG. 5C, the detection area can be set to the narrow area N as shown in FIG. 7. Also, if in place of the first adjusting cover 6 the second adjusting cover 7 shown in FIG. 10 is employed, the detection area can be set to the spot area S as shown in FIG. 7. Accordingly, in consideration of the environment in which the object detecting device is installed, the automatic door assembly can be so controlled as to cover the wide area W in the case where the automatic door assembly is in the form of a double door assembly 81 as shown in FIG. 6, or either one of the narrow area N and the spot area S smaller than the narrow area N in the case where the automatic door assembly is in the form of a single sliding door assembly 81A as shown in FIG. 7.

According to the foregoing construction, not only can the detection area be adjusted in leftward and rightward, forward and rearward directions, but also setting of the detection area to one of the wide area W shown in FIG. 6, the narrow area N and the spot area S, both shown in FIG. 7 can readily be accomplished easily and quickly at the site of installation of the object detecting device. In particular, since setting of the detection area to one of the wide area W and the narrow area N can be performed merely by turning the antenna module 4 shown in FIG. 2, the object detecting device embodying the present invention does not require the use of two dedicated antennas one for the wide area and the other for the narrow area as in the conventional object detecting device, thus reducing the number of component parts used therein. Accordingly, the object detecting device D compact in size and having an excellent handling capability can advantageously be assembled at a reduced cost. Also, the antenna AT can advantageously be protected by the adjusting covers 6 and 7 used one at a time.

Also, if the first holder 2 is turned about the first axis R1, the detection area in the leftward and rightward directions can be adjusted. On the other hand, if the second holder 3 is turned about the second axis R2, the detection area in the forward and rearward directions can be adjusted. Yet, if the antenna module 4 is turned about the third axis R3, the orientation of the antenna AT can be changed to enable the detection area to be set to one of the wide area W and the narrow area N. Thus, adjustment of the detection area about the three axes can easily be accomplished and, therefore, the installing operation can easily and quickly be performed at the site of installation.

It is to be noted that although in the foregoing embodiment reference has been made to the object detecting device having the three-axis adjustment capability, in which the detection area can be about the three axes R1 to R3, the present invention cannot be always limited to the type having the three-axis adjustment capability, but may be equally applied to the type having a two-axis adjustment capability or a single axis adjustment capability. Also, the antenna, which has been described as employed in the form of the wire in the foregoing embodiment, may be equally employed in the form of a patch antenna prepared from a metallic foil. In addition, the object detecting device of the present invention, which has been described as applied to the automatic door assembly, can equally be employed as a security sensor assembly for detecting an unauthorized entry of an intruder and then outputting a warning signal.

What is claimed is:

1. An object detecting device, which comprises:
    an antenna for emitting a detection wave towards a detection area and for receiving a portion of the detection wave reflected from an object; and
    an adjusting cover for covering the antenna and operable to adjust the detection area to one of different shapes, the adjusting cover being selectable from a plurality of adjusting covers to be fitted to the object detecting device one at a time.

2. The object detecting device as claimed in claim 1, wherein one of the adjusting covers comprises a disc shaped front wall and a peripheral wall extending rearwardly from a peripheral edge of the front wall, wherein the front wall has opposite side portions depressed radially inwardly to define corresponding cutouts for suppressing side lobes of the detection wave emitted from the antenna.

3. The object detecting device as claimed in claim 2, wherein another one of the adjusting covers comprises a disc shaped front wall and a peripheral wall extending rearwardly from a peripheral edge of the front wall, wherein the front wall has a convex lens portion having a thickness progressively increasing from a position of the peripheral edge thereof towards the geometric center of the front wall.

4. The object detecting device as claimed in claim 1, wherein the antenna is retained by a retaining member mounted rotatably on a sensor body and the adjusting cover is mounted on this retaining member.

5. The object detecting device as claimed in claim 1, further comprising:
    a support base;
    a first holder mounted on the support base for rotation about a first axis;
    a second holder supported under the first holder for rotation about a second axis lying perpendicular to the first axis; and
    an antenna module for retaining the antenna and mounted on the second holder for rotation about a third axis lying perpendicular to the second axis.

* * * * *